(12) United States Patent
Sørensen et al.

(10) Patent No.: US 11,476,007 B2
(45) Date of Patent: Oct. 18, 2022

(54) INFORMATION AND DATA LOGGING SYSTEM FOR USE IN A DENTAL ENVIRONMENT

(71) Applicant: XO Care A/S, Hørsholm (DK)

(72) Inventors: Leif Kim Sørensen, Klampenborg (DK); Peter Verner Bojsen Sørensen, Hørsholm (DK)

(73) Assignee: XO CARE A/S, Hørsholm (DK)

( * ) Notice: Subject to any disclaimer, the term of this patent is extended or adjusted under 35 U.S.C. 154(b) by 0 days.

(21) Appl. No.: 16/648,932

(22) PCT Filed: Jul. 9, 2018

(86) PCT No.: PCT/EP2018/074220
§ 371 (c)(1),
(2) Date: Mar. 19, 2020

(87) PCT Pub. No.: WO2019/057525
PCT Pub. Date: Mar. 28, 2019

(65) Prior Publication Data
US 2020/0286629 A1 Sep. 10, 2020

(30) Foreign Application Priority Data
Sep. 22, 2017 (EP) .................... 17192583

(51) Int. Cl.
G16H 40/20 (2018.01)
G16H 70/20 (2018.01)
A61C 1/00 (2006.01)
(52) U.S. Cl.
CPC ........... *G16H 70/20* (2018.01); *A61C 1/0007* (2013.01); *G16H 40/20* (2018.01)
(58) Field of Classification Search
CPC ....... G16H 70/20; G16H 40/20; A61C 1/0007
See application file for complete search history.

(56) References Cited

U.S. PATENT DOCUMENTS 7,085,607 B2 * 8/2006 Lipner ............... G05B 23/0272
700/32
10,925,511 B2 * 2/2021 Blake ....................... A61B 5/06
(Continued)

FOREIGN PATENT DOCUMENTS

| WO | 2004/080324 A1 | 9/2004 | |
| WO | WO-2004080324 A1 * | 9/2004 | ............... A61B 6/14 |
| WO | 2017/114688 A1 | 7/2017 | |

OTHER PUBLICATIONS

International Search Report issued in PCT/EP2018/074220 dated Dec. 12, 2018.

*Primary Examiner* — Jason S Tiedeman
*Assistant Examiner* — Liza Tony Kanaan
(74) *Attorney, Agent, or Firm* — Fox Rothschild LLP; Carol E. Thorstad-Forsyth

(57) ABSTRACT

Disclosed is an information and data logging system for use in a dental environment. The dental environment comprising a dental unit including a number of individual selectable dental instruments and at least one instrument control unit for controlling the operation of a selected dental instrument. The information and data logging system comprises: a processing unit; and one or more displays for displaying information related to a dental treatment and one or more input units, both the one or more displays and the one or more input units being operatively connectable to said processing unit. The processing unit is configured to enable a user to select using the one or more input units a selected alternative sequence of steps of one or more alternative sequences of steps.

15 Claims, 2 Drawing Sheets

(56) References Cited

U.S. PATENT DOCUMENTS

| | | | | |
|---|---|---|---|---|
| 2016/0210424 A1* | 7/2016 | Di Battista | ............ | G16H 10/60 |
| 2018/0271661 A1* | 9/2018 | Kamer | ................... | A61B 34/10 |
| 2019/0038367 A1* | 2/2019 | Ciriello | .............. | G05B 23/0272 |
| | | | | 700/32 |

* cited by examiner

INFORMATION AND DATA LOGGING SYSTEM FOR USE IN A DENTAL ENVIRONMENT

CROSS-REFERENCE TO RELATED APPLICATIONS

The present application is the U.S. National Phase of International Patent Application No. PCT/EP2018/074220, filed on Sep. 7, 2018 and entitled "INFORMATION AND DATA LOGGING SYSTEM FOR USE IN A DENTAL ENVIRONMENT," which claims priority to European Patent Application No. 17192583.7, filed on Sep. 22, 2017, the contents of which are incorporated herein by reference in their entireties.

FIELD

The present invention relates to an information and data logging system for use in a dental environment. The present invention further relates to a method of providing information and data logging in relation to a dental treatment.

BACKGROUND

Dental treatments typically include a number of sequential steps that must be performed for a successful result. Examples of dental treatments are filling treatments, root canal treatments, dental crown treatments, dental bridge treatments, implant treatments, and teeth whitening treatments.

The individual sequential steps are typically memorized by the dentist and performed without any technical assistance. Even thou dentist are skilled professionals the risk of human error is present. It may furthermore be challenging to share experience and best practice procedures.

WO 2004080324 discloses an information and control system for use in a dental environment having a dental unit with a number of selectable dental instruments and a control member for controlling their operation, a patient's rest and working positions for a dentist and a dental nurse. A computer is provided for storing treatment protocols listing selectable dental treatments, and for each treatment sequential steps to be performed in the treatment. Treatment and actions are displayed, and protocol control means are provided for inputting commands to the computer means for selection of treatments and actions listed in said protocols.

Thus, the dentist is provided with support when performing dental treatments.

However, it may be challenging for the dentist to select the correct treatment out of a significant number of possible treatments. It may furthermore be difficult to work with the system if an incorrect treatment is selected. Thus in practice the dentist will have to manually improvise to adapted the stored treatment protocol to the required treatment. This will reduce the precision of any generated data log.

US2016210424 discloses a computer-implemented method of assembling a medical treatment plan for a patient. The method includes presenting, by a computer system, a first treatment option and a second treatment option. At the computer system, receiving a first selection of the first treatment option and receiving a second selection of the second treatment option.

Thus by assembling building blocks the user may document a particular dental treatment.

It may however be complex and time consuming to select all the individual building blocks.

Thus, it remains a problem to provide an information and data logging system for use in a dental environment that is more flexible and easier to use.

SUMMARY

According to a first aspect, the invention relates to an information and data logging system for use in a dental environment, said dental environment comprising a dental unit including a number of individual selectable dental instruments and at least one instrument control unit for controlling the operation of a selected dental instrument, wherein said information and data logging system comprises: a processing unit; and one or more displays for displaying information related to a dental treatment and one or more input units, both said one or more displays and said one or more input units being operatively connectable to said processing unit; wherein said processing unit is configured to:

enable a user to select using said one or more input units a selected dental treatment of a plurality of dental treatments, each dental treatment of said plurality of dental treatment comprising a plurality of sequential steps;

control one of the one or more displays to show information relevant for performing a first step of said plurality of sequential steps of said selected dental treatment;

in response to having received a signal indicating that said user has completed said first step, control one of the one or more displays to show information relevant for performing a predetermined second step of said plurality of sequential steps of said selected dental treatment;

wherein said processing unit is further configured to, for said predetermined second step or a step subsequent to said predetermined second step, enable a user to select using said one or more input units a selected alternative sequence of steps of one or more chosen selectable alternative sequences of steps, the one or more selectable alternative sequence of steps being chosen dependent on both said selected dental treatment and the present step of said selected dental treatment, i.e. said predetermined second step or a step subsequent to said predetermined second step, the one or more selectable alternative sequences of steps comprising one or more steps, in response to the selection control one of the one or more displays to show information relevant for performing a first step of said selected alternative sequence of steps, and in response to having received a signal indicating that said user has completed and/or ended a dental treatment generating a data log specifying at least the selected dental treatment and all selected alternative sequence of steps.

Consequently, by enabling the user to select a selected alternative sequence of steps of one or more alternative sequences of steps a more flexible system is provided. This relives the dental care professional from the task of predicting the exact dental treatment needed before any treatment steps has been completed, i.e. the dental care professional may use information that becomes available after the treatment has been initiated to compose the complete treatment. Furthermore, the system enables a precise data log to be created for a specific dental treatment with only limited work required from the dental care professional.

A dental environment is the environment in which the dental care professionals work, i.e. the environment in which the dentist performs dental treatments on patients. A dental unit typically includes a dental chair for supporting the patient. The one or more input units may be a foot operated input unit, a touch screen, and/or a computer mouse. The step of selecting a selected dental treatment may comprises the steps of selecting a tooth and selecting a dental treatment for the selected tooth. The information relevant for performing a particular step (e.g. the first step, the second step, and/or subsequent steps) may comprise an indication of the dental instrument needed for performing the particular step, one or more words describing the particular step, a graphical representation indicating the particular step e.g. a graphical icon or a movie illustrating the particular step. The processing unit may be configured to enable a user to request additional information relevant for performing a particular step e.g. the processing unit may be configured to control one of the one or more displays to display first information relevant for performing a particular step and in response to having received a request from the user control one of the one or more displays to display second information relevant for performing the particular step. Each dental treatment may have associated specific alternative sequence of steps that are selectable only for said dental treatment. One or more of the specific alternative sequence of steps may be selectable for only a specific step of said dental treatment.

In some embodiments, the plurality of dental treatments comprises at least 1, 2, 3, 4, 5 or 6 of the following dental treatments:
  filling treatment;
  root canal treatment;
  dental crown treatment;
  dental bridge treatment;
  implant treatment; and
  teeth whitening treatment In some embodiments, said plurality of dental treatments comprises at least 3, 5 or 10 different dental treatments, and wherein each of said 3, 5 or 10 dental treatment has a unique set of alternative sequences of steps. In some embodiments, the processing unit is configured to enable a user to select using said one or more input units a selected alternative sequence of steps of a plurality of alternative sequences of steps including a first alternative sequence of steps and a second alternative sequence of steps, and wherein the first alternative sequence of steps includes the use of an instrument, material, and/or device, that is not used in the second alternative sequence of steps.

In some embodiments, one or more of the plurality of dental treatments has at least one sequential step where there are no alternative sequences of steps selectable.

Typically, there is no alternative sequences of steps selectable for at least the first step of each of the plurality of dental treatments since the dental care professional has not gained access to any knowledge and that stage.

In some embodiments, the processing unit is connectable to a data storage unit and configured to store the data log on the data storage unit.

The data storage unit may be a local data storage unit e.g. forming part of the system or a remote data storage unit e.g. on a server.

Consequently, by enabling the user to select alternative sequence of steps the data stored will more precisely reflect the performed treatment since the improvisation often need to perform a successful dental treatment may effectively be handled and thereby logged by the system.

In some embodiments, the data log further comprises data related to:

values of one or more control parameters for dental instrument used in the selected dental treatment;
  the time used for performing the sequential steps of the selected dental treatment; and/or
  the time used for performing the sequential steps of a selected alternative sequence of steps.

In some embodiments, said one or more chosen selectable alternative sequences of steps comprises a plurality of steps, and wherein said processing unit is further configured to in response to having received a signal indicating that said user has completed said first step of said selected alternative sequence of steps control one of the one or more displays to show information relevant for performing a predetermined second step of said selected alternative sequence of steps.

In some embodiments, the processing unit is configured to enable a user to select a selected alternative sequence of steps of said chosen selectable one or more alternative sequences of steps by being configured to:
  control one of the one or more displays to show a graphical element and/or text for each of the one or more alternative sequences of steps; and
  enable the user to select a graphical element and/or text using said one or more input units and thereby selected a selected alternative sequence of steps.

In some embodiments, the one or more alternative sequences of steps to be displayed are chosen dependent on an estimated probability of their selection.

Consequently, a more user-friendly and effective user interface may be provided.

The estimated probability may be pre-calculated and stored on a data storage unit. Additionally/alternatively, the estimated probability may be estimated by the processing unit based on previous choices made by the specific user and/or groups of users of the information and/or control system and/or other similar information and/or control systems.

In some embodiments, the information indicative of the one or more sequences of steps are arranged dependent on the estimated probability of their selection.

In some embodiments, at least one of said plurality of dental treatments comprises at least one step involving the use of a first dental instrument of said individual selectable instrument, said first dental instrument being connectable to said processing unit, and wherein said processing unit is further configured to set predetermined values of one or more control parameters for said first dental instrument for the use of said first dental instrument in said at least one step.

The first dental instrument may be connectable to said processing unit by being connected to the instrument control unit connected to the processing unit. Alternatively, the first dental instruments may be directly connected to the processing unit i.e. the processing unit of the information and control system and the instrument control unit of the dental environment may be integrated in a single processing unit. Examples of dental instruments are: a micro motor (e.g. for a drill), a syringe, a curing light, a camera, an air instrument (turbine), a curing light, a scaler, and intraoral camera. A typical dental treatment will require the use of a number of different dental instruments for the individual steps. Thus, predetermined values of one or more control parameters may be set for a plurality of dental instruments for their respective steps.

In some embodiments, said processing unit is operatively connectable to said individual selectable instruments via said instrument control unit and further configured to lock dental instruments not intended to be used for a present step whereby the user may be prevented from accidentally using a wrong instrument for the present step.

Consequently, a more secure system is provided.

The processing unit may be configured to un-lock the locked dental instrument after the user has confirmed his/her intent to use the dental instrument.

In some embodiments, said first step involve the use of a first dental instrument, said second step involves the use of a second dental instrument, and said first step of said selected alternative sequence of steps involve the use of a third dental instrument, said first dental instrument, said second dental instrument, and said third dental instrument being connectable to said processing unit and wherein said processing unit further is configured to:
- to set predetermined values of one or more control parameters for said first dental instrument, said predetermined values being adapted to said first step of said selected dental treatment:
- to set predetermined values of one or more control parameters for said second dental instrument, said predetermined values being adapted to said second step of said selected dental treatment;
- to set predetermined values of one or more control parameters for said third dental instrument, said predetermined values being adapted to said first step of said selected alternative sequence of steps.

In some embodiments, one of said chosen selectable plurality of alternative sequences of steps is a default sequence of steps, and wherein said one or more input unit has a first button that when it is activated signals to the processing unit that the present step has been completed, and wherein the first button may furthermore be used to select said default sequence of steps.

Consequently, the extra flexibility provided by enabling the user to select between multiple sequences of steps can be implemented without increasing the complexity of the system.

The first button may be a button on a foot operated input unit, a physical button on an instrument holder, or a button on a touch screen.

In some embodiments, the processing unit is configured to prompt the user to make a clinical decision, and wherein said clinical decision is used in the selection of said selected alternative sequence of steps.

The user may be prompted to indicate a material, surgical component, and/or a dental instrument to be used in the next step or in a subsequent step. Alternatively/additionally, the user may be asked to answer a clinical question.

The clinical decision may directly be used to select a selected alternative sequence of steps. Alternatively, the processing unit may be configured to present to the user one or more alternative sequences of steps on one of said one or more displays based on the clinical decision and furthermore allow the user to select one of the displayed alternative sequences of steps.

Consequently, the dental care professional may be forced to make a specific clinical decision in the process of selecting an alternative sequence of steps.

According to a second aspect, the invention relates to a method of providing information to a user and data logging in relation to a dental treatment, the method comprising the steps of:
- enabling a user to select using one or more input units a selected dental treatment of a plurality of dental treatments, each dental treatment of said plurality of dental treatment comprising a plurality of sequential steps;
- controlling one of one or more displays to show information relevant for performing a first step of said plurality of sequential steps of said selected dental treatment;
- in response to having received a signal indicating that said user has completed said first step, controlling one of the one or more displays to show information relevant for performing a predetermined second step of said plurality of sequential steps of said selected dental treatment;

wherein for said predetermined second step or a step subsequent to said predetermined second step, the method further comprises the step of:
- enabling a user to select using said one or more input units a selected alternative sequence of steps of one or more chosen selectable alternative sequences of steps, the one or more selectable alternative sequence of steps being chosen dependent on both said selected dental treatment and the present step of said selected dental treatment, i.e. said predetermined second step or a step subsequent to said predetermined second step, the one or more selectable alternative sequences of steps comprising one or more steps, and in response to the selection control one of the one or more displays to show information relevant for performing a first step of said selected alternative sequence of steps; and
- in response to having received a signal indicating that said user has completed and/or ended a dental treatment generating a data log specifying at least the selected dental treatment and all selected alternative sequence of steps.

In some embodiments, the processing unit is configured to enable a user to select using said one or more input units a selected alternative sequence of steps of a plurality of chosen selectable alternative sequences of steps including a first alternative sequence of steps and a second alternative sequence of steps, and wherein the first alternative sequence of steps includes the use of an instrument, material, and/or device, that is not used in the second alternative sequence of steps.

In some embodiments, one or more of the plurality of dental treatments has at least one sequential step where there are no alternative sequences of steps selectable.

In some embodiments, the method further comprises the step of storing said data log a data storage unit.

In some embodiments, said data log further comprise data related to:
- values of one or more control parameters for dental instrument used in the selected dental treatment; and/or
- the time used for performing the sequential steps of the selected dental treatment.

In some embodiments, said one or more chosen selectable alternative sequences of steps comprises a plurality of steps, and wherein after the user has indicated that the first step has been completed, the method further comprises the step of:
- control one of the one or more displays to show information relevant for performing a predetermined second step of said selected alternative sequence of steps.

In some embodiments, the step of enabling a user to select a selected alternative sequence of steps of one or more chosen selectable alternative sequences of steps, comprises the steps of:
- controlling one of the one or more displays to show a graphical element and/or text for each of the one or more alternative sequences of steps; and enabling the user to select a graphical element and/or text using said one or more input units and thereby selected a selected alternative sequence of steps.

In some embodiments, the one or more chosen selectable alternative sequences of steps to be displayed are chosen dependent on an estimated probability of their selection.

In some embodiments, the information indicative of the one or more sequences of steps are arranged dependent on the estimated probability of their selection.

In some embodiments, at least one of said plurality of dental treatments comprises at least one step involving the use of a first dental instrument of said individual selectable instrument and wherein predetermined values of one or more control parameters are set for said first dental instrument for performing said at least one step.

In some embodiments, dental instruments not intended to be used for a present step are locked whereby the user may be prevented from accidentally using a wrong instrument for the present step.

In some embodiments, said first step involve the use of a first dental instrument, said second step involves the use of a second dental instrument, and said first step of said selected alternative sequence of steps involve the use of a third dental instrument, wherein said method further comprises:
setting values of one or more control parameters for said first dental instrument, said predetermined values being adapted to said first step of said selected dental treatment:
setting values of one or more control parameters for said second dental instrument, said predetermined values being adapted to said second step of said selected dental treatment; and
setting values of one or more control parameters for said third dental instrument, said predetermined values being adapted to said first step of said selected alternative sequence of steps.

In some embodiments, one of said plurality of chosen selectable alternative sequences of steps is a default sequence of steps, and wherein said one or more input unit has a first button that when it is activated signals that the present step has been completed, and wherein the first button may furthermore be used to select said default sequence of steps.

In some embodiments, the user is being prompted to make a clinical decision, and wherein said clinical decision is used in the selection of said selected alternative sequence of steps.

According to a thirds aspect, the invention relates to a computer program product comprising program code means adapted to cause a data processing system to perform the steps of the method disclosed in the connection to the second aspect of the invention.

In some embodiments, said computer program product comprises a non-transitory computer-readable medium having stored thereon the program code means.

According to fourth aspect, the invention relates to a computer program product comprising program code means adapted to cause an information and/or control system to perform the steps of the method disclosed in the connection to the second aspect of the invention, wherein said information and/or control system is for use in a dental environment, said dental environment comprising a dental unit including a number of individual selectable dental instruments and at least one instrument control unit for controlling the operation of a selected dental instrument, wherein said information and/or control system comprises: a processing unit; and one or more displays for displaying information related to a dental treatment and one or more input units, both said one or more displays and said one or more input units being operatively connectable to said processing unit.

In some embodiments, said computer program product comprises a non-transitory computer-readable medium having stored thereon the program code means.

The different aspects of the present invention can be implemented in different ways including as an information and/or control system, and a method of providing information and/or providing control signals described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
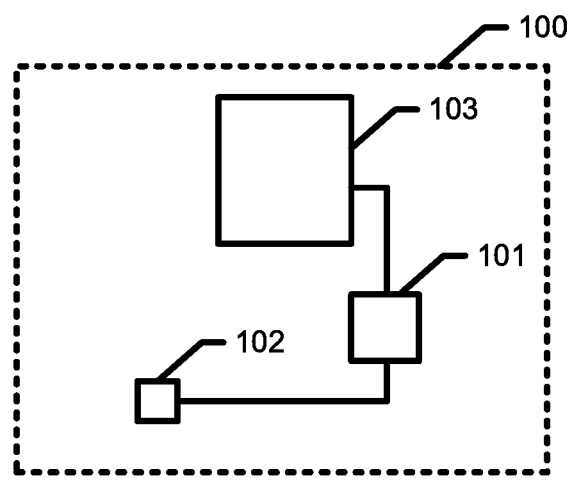
FIG. 1 shows a schematic drawing of an information and/or control system for use in a dental environment according to an embodiment of the present invention.

FIG. 1 shows a schematic drawing of an information and data logging system 100 for use in a dental environment according to an embodiment of the present invention. The system 100 comprises a procession unit 101, an input unit 102, and a display 103. The display 103 and the input unit 102 are both operatively connected to the processing unit 101. In this embodiment, the input unit 102 is separate from the display 103, however in other embodiments the two may be combined in a single unit e.g. in a touch screen. The processing unit is configured to enable a user to select using the input unit 102 a selected dental treatment of a plurality of dental treatments, each dental treatment of the plurality of dental treatment comprising a plurality of sequential steps. As an example the user may indicate that the patient needs a filling treatment. The user may be enabled to select a dental treatment by being presented with a plurality of dental treatments on the display 103. In response to the selection, the processing unit 101 is further configured to control the display to show information relevant for performing a first step of the plurality of sequential steps of the selected dental treatment. As an example the display 103 may show one or more words describing the first step e.g. the word "anaesthesia" may be displayed indicating that the patient should be provided with anaesthesia in the first step. Alternatively/ additionally, the display 103 may indicate a dental instrument to be used in the first step. In response to having received a signal indicating that said user has completed the first step, the processing unit 101 is configured control the display 103 to show information relevant for performing a predetermined second step of the plurality of sequential steps of the selected dental treatment. As an example the user may use the input unit 102 to indicate that the first step has been completed e.g. by pushing a button on the input unit 102. As an example the display 103 may show one or more words describing the second step e.g. the word "excavation" may be displayed indicating that a tooth should be excavated in the next step. Additionally/alternatively, the display 103 may indicate that a micro motor fitted with a dental drill should be used for excavating a tooth. In some embodiments, the processing unit 101 is operatively connected to one or more dental instruments and configured to set pre-determined values of one or more control parameters for a dental instrument for a particular sequential step e.g. the processing unit may set the rotational speed of a micro motor or the max torque. For at least one step e.g. the second step or a subsequent step, the processing unit 101 is further configured to enable a user to select using the input unit 102 a selected alternative sequence of steps of a plurality chosen selectable of alternative sequences of steps, the one or more selectable alternative sequence of steps being chosen dependent on both said selected dental treatment and the present step of said selected dental treatment, i.e. said predetermined second step or a step subsequent to said predetermined second step, each of the plurality of selectable alternative sequences of steps comprising one or more steps, and in response to the selection control one of the one or more displays to show information relevant for performing a first step of the selected alternative sequence of steps. As an example, after the second sequential step, the user may be prompted to make a clinical decision e.g. by indicating a filling material to be used for a tooth filing. The user may be presented with a list of possible filling materials on the display 103 and being asked to select a filling material using the input unit 102. The clinical decision may directly result in the selection of an alternative sequence of steps or aid in the selection. Finally, once the processing unit 101 has received a signal indicating that said user has completed and/or ended a dental treatment it creates a data log specifying at least the selected dental treatment and all selected alternative sequence of steps.

Consequently, the user may use information that becomes available after the treatment has been initiated in the composition of the complete treatment.

Figure 2:
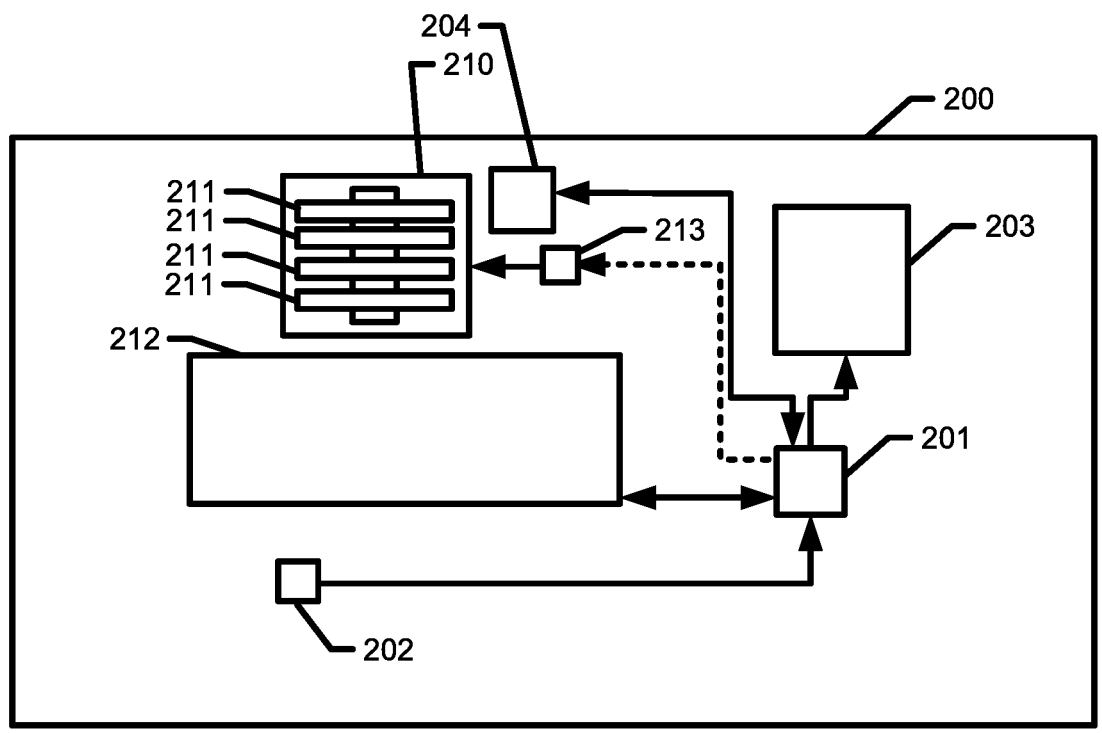
FIG. 2 shows a dental environment comprising an information and/or control system according to an embodiment of the present invention.

FIG. 2 shows a dental environment 200 comprising an information and/or control system according to an embodiment of the present invention. The dental environment comprises a dental unit including a number of individual selectable dental instruments 211 arranged on an instrument holder 210, an instrument control unit 213 for controlling the operation of the dental instruments 211 and a dental chair 212 for supporting a patient. The information and/or control system comprises a processing unit 201, a first display 203, a second display 204, and a first input unit 202. The processing unit 201 is operatively connected to the first display 203, the second display 203, and the first input unit 202. The processing unit may further be operatively connected to the instrument control unit 213, whereby operation of the individual selectable dental instruments may be controlled by the processing unit 201 e.g. the processing unit may set the value of one or more control parameters for some or all of the individually selectable dental instruments 211. The instrument control unit 213 and the processing unit 201 may be integrated in a single processing unit. The second display 204 may be a touchscreen and thereby function as a second input unit. The information and/or control system may be an integral part of the dental unit or provided separate from the dental unit.

Figure 3:
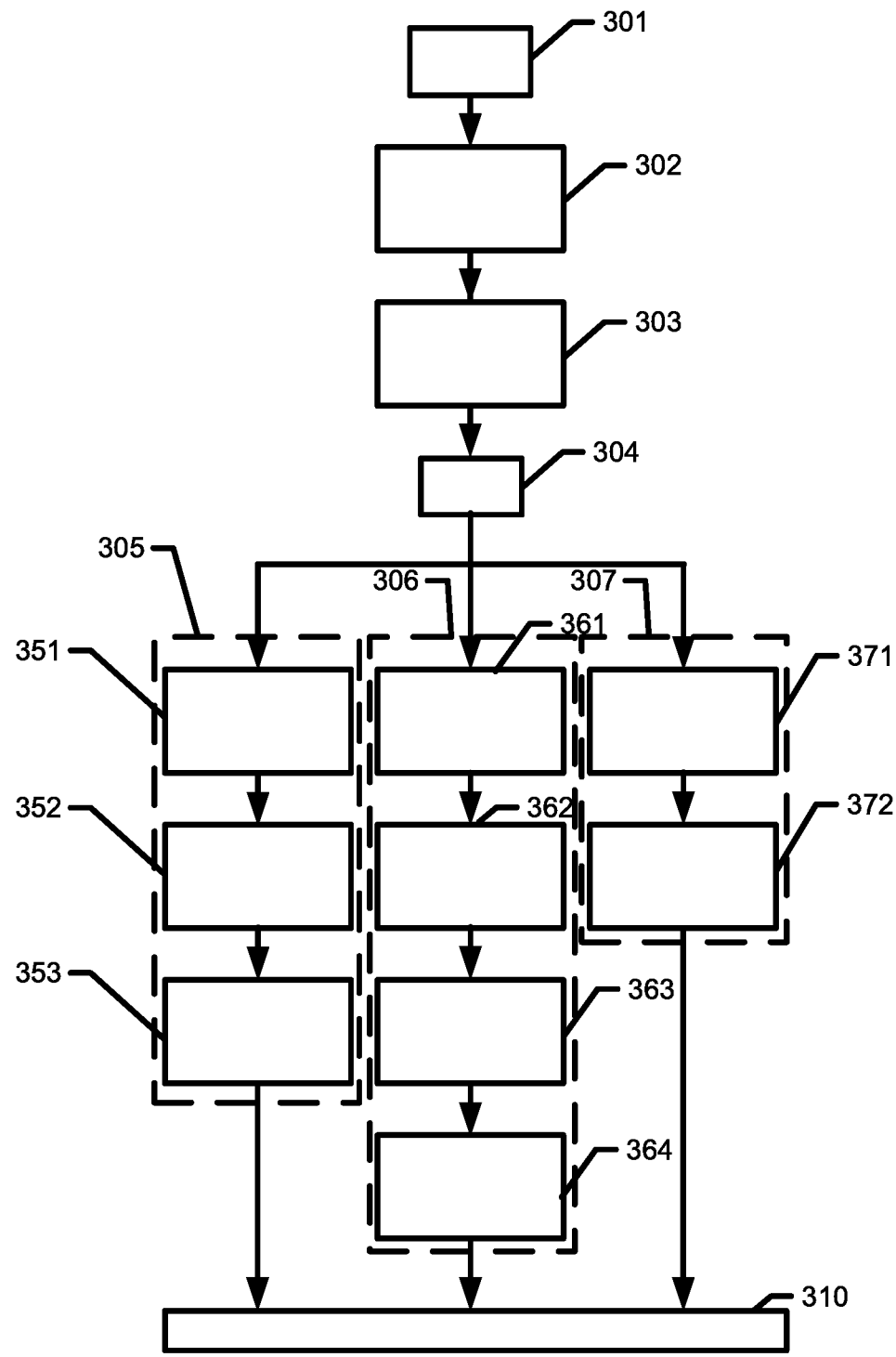
FIG. 3 shows a flowchart of a method of providing information and/or providing control signals to dental instruments in relation to a dental treatment, according to an embodiment of the present invention.

FIG. 3 shows a flowchart of a method of providing information and data logging in relation to a dental treatment, according to an embodiment of the present invention. The method starts in step 301 with enabling a user to select using one or more input units a selected dental treatment of a plurality of dental treatments, each dental treatment of the plurality of dental treatment comprising a plurality of sequential steps. Next, in step 302, one of one or more displays is controlled to show information relevant for performing a first step of the plurality of sequential steps of the selected dental treatment. Then, in step 303 one of the one or more displays is controlled in response to having received a signal indicating that said user has completed the first step to show information relevant for performing a predetermined second step of the plurality of sequential steps of the selected dental treatment. Next, in step 304 the user is enabled to select using the one or more input units a selected alternative sequence of steps of one or more chosen selectable alternative sequences of steps 305 306 307, the one or more selectable alternative sequence of steps being chosen dependent on both the selected dental treatment and the present step of the selected dental treatment, i.e. the predetermined second step. In this embodiment, the user can select between three alternative sequences of steps 305 306 307. In this embodiment, the user can only select between the three alternative sequences of steps 305 306 307 after having completed the second step of the selected dental treatment. However, in other embodiments, the user may select between one or more alternative sequence of steps after having completed the first step of the dental treatment or any subsequent step of the dental treatment. In this embodiment, the alternative sequences of step 305 comprises three sequential steps 351-353, the alternative sequence of step 306 comprises four sequential steps 361-364, and the alternative sequence of steps 307 comprises two sequential steps 371-372. In response to the selection, one of the one or more displays is controlled to show information relevant for performing a first step of the selected alternative sequence of steps. Thus, if the user selects the alternative sequence of steps 305 one of the one or more displays is controlled to show information relevant for performing the step 351, if the user selects the alternative sequence of steps 306 one of the one or more displays is controlled to show information relevant for performing the step 361, and if the user select the alternative sequence of steps 307 one of the one or more displays is controlled to show information relevant for performing the step 371. Each alternative sequence of steps 305-307 may use a unique combination of dental instruments, materials, and/or surgical components, i.e. the alternative sequence of steps 305 may use a combination of dental instruments, materials, and/or surgical components different from the alternative sequences of steps 306 and 307 and the alternative sequence of steps 306 may use a combination of dental instruments, materials, and/or surgical components different from the alternative sequence of steps 307. Finally, in step 310, in response to having received a signal indicating that said user has completed and/or ended a dental treatment a data log is generated specifying at least the selected dental treatment and all selected alternative sequence of steps.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A system for controlling operations of a plurality of dental instruments, comprising:
   a processor connected to the plurality of dental instruments, the plurality of dental instruments being controlled based on one or more control parameters;
   one or more display devices connected to the processor and configured to display information related to a dental treatment; and
   one or more input devices operatively connected to said processor and configured to facilitate user-software interactions with the system; wherein said processor is configured to:
   facilitate a first user-software interaction for selecting a dental treatment of a plurality of dental treatments via the one or more input devices, each said dental treatment of said plurality of dental treatments comprising a plurality of sequential steps for controlling operations of the system, and a plurality of pre-programmed alternative sequence of steps;
   control one of the one or more display devices to show information relevant for performing a first step of said plurality of sequential steps of said dental treatment, when said dental treatment is selected by a user via the first user-software interaction;
   automatedly control operations of a first dental instrument in accordance with control parameters associated with the first step in said dental treatment;
   in response to having received a signal indicating that said first step has been completed, control one of the one or more display devices to show information relevant to performance of a predetermined second step of said plurality of sequential steps of said dental treatment;
   wherein said processor is further configured to for a predetermined step, being said predetermined second step or a step subsequent to said predetermined second step,
   facilitate a second user-software interaction for selecting a pre-programed alternative sequence of steps of the plurality of pre-programmed alternative sequence of steps of the dental treatment, and
   automatedly control operations of a second dental instrument of the plurality of dental instruments in accordance with control parameters associated with a step of the pre-programmed alternative sequence of steps;
   in response to having received a signal indicating that the dental treatment has been completed, generate a data log specifying at least the dental treatment and the pre-programmed alternative sequence of steps.

2. A system according to claim 1, wherein said alternative sequence of steps comprises a plurality of steps, and wherein said processor is further configured to, in response to having received a signal indicating that said user has completed said step of said alternative sequence of steps, control one of the one or more display devices to show information relevant to a performance of another step of said pre-programmed alternative sequence of steps.

3. A system according to claim 1, wherein said second step of said plurality of sequential steps of said dental treatment involves the use of a third dental instrument which is different than the first and second dental instruments, and said processor is configured to
   set predetermined values of one or more control parameters for said third dental instrument in accordance with said pre-programmed alternative sequence of steps.

4. A system according to claim 1, wherein one of said plurality of pre-programmed alternative sequences of steps is a default sequence of steps, and wherein said one or more input devices has a first button that when it is activated signals to the processor that the present step has been completed, and wherein the first button is furthermore used to select said default sequence of steps.

5. A system according to claim 1, wherein the processor is configured to prompt the user to make a clinical decision, and wherein said clinical decision is used in the selection of said pre-programmed alternative sequence of steps.

6. A system according to claim 1, wherein one or more of the plurality of dental treatments has at least one sequential step where there are no alternative sequences of steps selectable.

7. A system according to claim 1, wherein the processor is connectable to a data store and configured to store the data log on the data store.

8. A method for providing a dental treatment, comprising:
   facilitating a first user-software interaction for selecting a dental treatment of a plurality of dental treatments via an input device, each said dental treatment of said plurality of dental treatment comprising a plurality of sequential steps and a plurality of pre-programmed alternative sequence of steps;
   controlling one of one or more display devices to show information relevant for performing a first step of said plurality of sequential steps of said dental treatment, when said dental treatment is selected by a user via the first user-software interaction;
   automatedly controlling operation of a first dental instrument in accordance with control parameters associated with the first step in said dental treatment;
   in response to having received a signal indicating that said first step has been completed, controlling one of the one or more display devices to show information relevant to performance of a predetermined second step of said plurality of sequential steps of said dental treatment;
   wherein fora predetermined step, being said predetermined second step or a step subsequent to said predetermined second step, the method further comprises:
   facilitating a second user-software interaction for selecting a pre-programmed alternative sequence of steps of a plurality of pre-programmed alternative sequence of steps of the dental treatment;
   automatedly controlling operations of a second dental instrument of the plurality of dental instruments in accordance with control parameters associated with a step of the pre-programmed alternative sequence of steps; and in response to having received a signal indicating that the dental treatment has been completed, generating a data log specifying at least the dental treatment and the pre-programmed alternative sequence of steps.

9. A method according to claim 8, wherein said alternative sequences of steps comprises a plurality of steps, and wherein after the first step has been completed, the method further comprises:

controlling one of the one or more display devices to show information relevant for performing a second step of said pre-programmed alternative sequence of steps.

10. A method according to claim 8, wherein operations of the first dental instrument are automatically controlled by setting at least one of said control parameters to a value required for performing said first step of said plurality of sequential steps of said dental treatment.

11. A method according to claim 10, wherein said second step of said plurality of sequential steps of said dental treatment involves the use of a third dental instrument, wherein said method further comprises:

setting values of one or more control parameters for said third dental instrument in accordance with said pre-programmed alternative sequence of steps.

12. A method according to claim 8, wherein one of said plurality of pre-programmed alternative sequences of steps is a default sequence of steps, and wherein said one or more input devices has a first button that when it is activated signals that the present step has been completed, and wherein the first button is furthermore used to select said default sequence of steps.

13. A method according to claim 8, further comprising prompting the user prompted to make a clinical decision, and wherein said clinical decision is used in the selection of said alternative sequence of steps.

14. A method according to claim 8, wherein the method further comprises storing said data log on a data store.

15. A computer program product comprising a memory and programming instructions that are configured to cause a processor to perform the method according to claim 8.

* * * * *